United States Patent [19]

Billings

[11] 4,072,718

[45] Feb. 7, 1978

[54] METHODS OF CONVERTING DITERTIARY ORGANIC SULFIDES TO DITERTIARY ORGANIC DISULFIDES

[75] Inventor: William G. Billings, Bartlesville, Okla.

[73] Assignee: Phillips Petroleum Company, Bartlesville, Okla.

[21] Appl. No.: 706,421

[22] Filed: July 19, 1976

[51] Int. Cl.² .......................................... C07C 149/12
[52] U.S. Cl. ................. 260/608; 260/590 R; 260/593 R; 260/599; 260/601 R; 560/152; 560/153; 560/154; 560/15
[58] Field of Search ................. 260/608, 481 R, 470, 260/590 R, 593 R, 599, 601 R

[56] References Cited

U.S. PATENT DOCUMENTS

| | | | |
|---|---|---|---|
| 2,503,644 | 4/1950 | Warner et al. | 260/608 |
| 3,022,351 | 2/1962 | Mihin et al. | 260/608 |
| 3,340,324 | 9/1967 | Warner | 260/608 |
| 3,387,039 | 6/1968 | Doss | 260/608 |
| 3,397,244 | 8/1968 | Louthan | 260/609 |
| 3,531,160 | 9/1970 | Fisher | 299/5 |
| 3,586,723 | 6/1971 | Alley et al. | 260/608 |
| 3,755,461 | 3/1972 | Kvasnikoff et al. | 260/608 |

OTHER PUBLICATIONS

Journal of Organic Chemistry, 28, 3246–3247 (1963).
Journal of Organic Chemistry, 23, 2028–2029 (1958).
E. E. Reid, Organic Chemistry of Bivalent Sulfur, vol. II, Chemical Publishing Co., Inc., N.Y., 1960, p. 61.
Journal of Organic Chemistry, 40 (21), 3152–3154 (1975).

*Primary Examiner*—Joseph Paul Brust
*Assistant Examiner*—Molly C. Eakin

[57] ABSTRACT

Ditertiary organic disulfides are produced by contacting at least one ditertiary organic sulfide with at least one suitable hydrocarbyl sulfoxide and a catalyzing amount of a protonic acid.

16 Claims, No Drawings

METHODS OF CONVERTING DITERTIARY ORGANIC SULFIDES TO DITERTIARY ORGANIC DISULFIDES

BACKGROUND OF THE INVENTION

1. Field of the Invention

This invention concerns the preparation of ditertiary organic disulfides from ditertiary organic sulfides.

2. Description of the Prior Art

Generally, organic disulfides and polysulfides are produced from thiol compounds. Typical examples of such methods of producing organic polysulfides or disulfides are shown in the following patents: U.S. Pat. Nos. 2,503,644; 3,022,351; 3,340,324; 3,387,039; 3,397,244; 3,586,723; and 3,755,461. Also, *J. Org. Chem.* 28, 3246–3247 (1963) discloses the production of organic disulfides by the oxidation of a thiol with dimethyl sulfoxide.

In accordance with the present invention, ditertiary organic disulfides are produced from ditertiary organic sulfides.

Accordingly, it is an object of this invention to provide a method for preparing ditertiary organic disulfides from ditertiary organic sulfides.

A further object of this invention is to provide a method of preparing ditertiary alkyl disulfides from the corresponding ditertiary alkyl sulfides.

Other aspects, objects, as well as the advantages of the invention will be apparent from this disclosure and the appended claims.

According to this invention ditertiary organic disulfides can be prepared by contacting under suitable reaction conditions at least one ditertiary organic sulfide and at least one hydrocarbyl sulfoxide in the presence of a reaction promoting amount of at least one protonic acid.

The term ditertiary organic sulfide denotes those sulfides having the formula

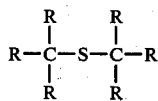

wherein each R may be the same or different radical selected from the group consisting of hydrocarbyl radicals and substituted hydrocarbyl radicals. The term substituted hydrocarbyl radicals denotes those hydrocarbyl radicals that contain suitable substituents containing elements other than carbon and hydrogen. Examples of suitable substituents include

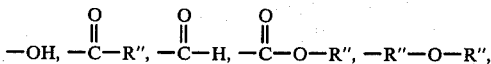

and halogens, where R″ is again a hydrocarbyl radical having from 1 to 12 carbon atoms. The preferred ditertiary organic sulfides are those in which each R is individually selected from hydrocarbyl radicals having from 1 to 12 carbon atoms. Examples of such ditertiary organic sulfides include ditertiary butyl sulfide, ditertiary amyl sulfide, ditertiary octyl sulfide, ditertiary tetradecyl sulfide, (di(1,1-diethyl ethyl)sulfide, di(1,1-dimethyl-1-phenyl methyl)sulfide, tertiary butyl-tertiary octyl sulfide, tertiary butyl-1,1-dimethyl-1-phenyl methyl sulfide, and the like and mixtures of any two or more thereof. Especially preferred ditertiary organic sulfide reactants are those in which each R is an alkyl radical having from 1 to 12 carbon atoms.

When the two tertiary groups in a ditertiary organic sulfide are not the same there is the possibility to obtain three different disulfide products, one containing both tertiary groups, one in which both organic substituents are identical to one of the tertiary groups in the reactant, and another in which both organic substituents are identical to the other of the tertiary groups in the reactant.

The hydrocarbyl sulfoxides suitable for use in this invention are those of the formula

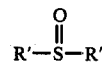

wherein each R′ may be the same or different alkyl radical having from 1 to 12 carbon atoms or wherein the two such R′ alkyl groups are combined by a bond to form a cyclic ring containing at least 4 carbons in the cyclic ring in addition to the sulfur atom. Examples of such hydrocarbyl sulfoxides include dimethyl sulfoxide, diethyl sulfoxide, methyl ethyl sulfoxide, didodecyl sulfoxide, tetramethylene sulfoxide, and mixtures of any two or more thereof.

Any suitable protonic acid can be used to promote the reaction herein disclosed. Examples of protonic acids include hydrochloric acid, hydrobromic acid, hydroiodic acid, hydrofluoric acid, sulfuric acid, nitric acid, acetic acid, propionic acid, trichloroacetic acid, chlorosulfuric acid, phthalic acid, benzenesulfonic acid, and the like and mixtures of any two or more thereof. Especially preferred protonic acids are hydrochloric, hydrobromic, and hydroiodic acids.

The employment of a small amount of at least one suitable Lewis acid in conjunction with the protonic acid can increase the rate of the reaction. Suitable Lewis acids include, for example, lead chloride, zinc chloride, aluminum chloride, tin tetrachloride, boron trifluoride, magnesium bromide, lead bromide, and the like and mixtures of any two or more thereof.

Any suitable amounts of ditertiary organic sulfide and hydrocarbyl sulfoxide can be reacted. Generally, however, the molar ratio of hydrocarbyl sulfoxide to ditertiary organic sulfide is in the range of about 20/1 to about 1/20, preferably in the range of about 5/1 to about 2/1.

Although it is not necessary, it is preferred that the contacting of ditertiary organic sulfide and hydrocarbyl sulfoxide be conducted in the presence of a diluent. Suitable diluents include any organic liquid that is inert under the reaction conditions. Examples of suitable diluents include monohydric alcohols, for example, benzol, methanol, ethanol, butanol, and the like; ethers of the type R″ — O — R‴ where R″ and R‴ may be the same or different alkyl or aryl radicals, for example, diethyl ether, dipropyl ether, di-n-butyl ether, diphenyl ether, and the like, hydrocarbons, for example, benzene, toluene, heptane, hexane, and the like, or mixtures of any two or more inert diluents such as those set forth. The preferred diluents are saturated aliphatic monohydric alcohols having 1 to 8 carbon atoms. Any suitable amount of diluent can be employed. Generally the number of moles of diluent is no greater than about 10 times the sum of the moles of ditertiary organic sulfide and hydrocarbyl sulfoxide and no less than about 0.01 of that sum. Preferably the number of moles of diluent is no greater than about 5 times the sum of the moles of ditertiary organic sulfide and alkyl sulfoxide and no less than about 0.1 of that sum.

The protonic acid can be employed in any amount that promotes the production of ditertiary organic disulfide. Generally the ratio of the moles of protonic acid to the sum of the moles of the hydrocarbyl sulfoxide and ditertiary organic sulfide is in the range of about 0.0001/1 to about 0.01/1, preferably in the range of about 0.001/1 to about 0.003/1.

Lewis acid, when employed, is employed in any amount that increases the rate of the reaction. Generally the ratio of the moles of Lewis acid to the sum of the moles of the hydrocarbyl sulfoxide and ditertiary organic sulfide will be in the range of about 0.001/1 to about 0.1/1, preferably in the range of about 0.005/1 to about 0.05/1.

Any suitable temperature conditions can be employed in the present invention. Generally the temperature is in the range of about 40° C. to about 250° C., preferably in the range of about 50° C. to about 150° C. When higher temperatures are used the yield of disulfide is reduced by the formation of increasing amounts of higher organic polysulfides, i.e., trisulfides and tetrasulfides.

Any suitable pressure conditions can be employed. It is preferred to conduct the reaction at atmospheric pressure. To limit the possibility of undesired side reactions it is also preferred to conduct the reaction under an inert atmosphere.

The following examples are to be construed as merely illustrative, and not unduly limitative of the remainder of the specification and claims.

EXAMPLE I

Twenty milliliters of a solution containing 61.8 mol percent methanol, 31.4 mol percent dimethyl sulfoxide, 5.45 mol percent di-t-butyl sulfide and 1.57 mol percent dibenzothiophene was charged to a pyrex vessel and the vessel was purged with helium. (The bidenzothiophene was included as a compound that would be unaffected by the reaction so as to serve as a standard which would enable one to determine the mol percent of the products by gas-liquid chromatography.) The vessel was then charged with 0.25 ml of concentrated hydrochloric acid and 0.2 grams of lead chloride. The resulting mixture was then heated. A flow of helium of 5 cc/minute was continued throughout the run. Aliquot portions were withdrawn from the reaction mixture at intervals and analyzed by means of gas-liquid chromatography. The reaction conditions and product analyses are summarized in Table I. In Table I the term "neg." indicates that no measurable amount was observed.

TABLE I

| Reaction Time (Minutes) | Reaction Temperature, ° C. | Product, Mol Percent di-t-Butyl Sulfide | di-t-Butyl Disulfide |
|---|---|---|---|
| 0 | 21 | 5.45 | neg. |
| 10 | 43 | 4.7 | 0.4 |
| 20 | 71 | 3.1 | 1.2 |
| 35 | 74 | 0.5 | 2.3 |
| 45 | 74 | 0.3 | 2.4 |
| 60 | 74 | 0.1 | 2.5 |
| 75 | 74 | neg. | 2.5 |

The data in Table I show that after 75 minutes substantially all the di-t-butyl sulfide was used up and that the amount of di-t-butyl disulfide produced was equivalent to a 92 percent conversion of the di-t-butyl sulfide to di-t-butyl disulfide.

EXAMPLE II

A solution containing 37.3 mol percent dimethyl sulfoxide, 7.2 mol percent di-t-butyl sulfide, 55 mol percent methanol, and 0.3 mol percent dibenzothiophene was prepared.

Heating approximately 20 ml of this solution for 1.5 hours at 220° F. (104° C.) did not result in any apparent reaction.

However, when 8 drops of concentrated hydrochloric acid was added to 20 ml of the solution, heating at 220° F. (104° C.) for 1.5 hours resulted in a nearly quantitative yield of polysulfides such as disulfides and trisulfides.

When a small amount (less than about 0.3 g) of lead chloride was added to 20 ml of the solution no disulfide product was observed after the solution was heated for 1.5 hours at 220° F. (104° C.).

This example demonstrates the necessity of employing a protonic acid as a catalyst in the present invention.

EXAMPLE III

Heating 10 ml of di-t-butyl sulfide at 300° F. (149° C.) for about 3 hours gave no observable production of di-t-butyl disulfide.

Heating 10 ml of di-t-butyl sulfide at 300° F. (149° C.) in the presence of catalytic amounts of zinc chloride and hydrochloric acid gave a mixture of decomposition products; however, gas-liquid chromatography showed no evidence of di-t-butyl disulfide.

When a mixture of 10 ml of di-t-butyl sulfide and 2.5 ml of dimethyl sulfoxide was heated at 300° F. (149° C.) for about 40 minutes in the presence of catalytic amounts of hydrochloric acid and zinc chloride a 42 percent yield of di-t-butyl disulfide was obtained, as indicated by gas-liquid chromatography.

When a mixture of 10 ml of di-t-butyl sulfide and 10 ml of dimethyl sulfoxide was heated at 300° F. (149° C.) for about 40 minutes in the presence of catalytic amounts of zinc chloride and hydrochloric acid, gas-liquid chromatography indicated an 85 percent yield of di-t-butyl disulfide. The identity of the product was confirmed by mass spectrometry and infrared spectroscopy.

From the foregoing description and examples, one skilled in the art can easily ascertain the essential characteristics of this invention and without departing from the spirit and scope thereof, can make various changes and modifications of the invention to adapt it to various usages and conditions. Consequently, such changes and modifications are properly, equitably, and intended to be, within the full range of equivalence of the following claims.

What is claimed is:

1. A method comprising contacting at least one ditertiary organic sulfide of the formula

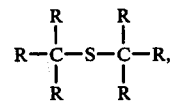

wherein each R may be the same or different radical selected from hydrocarbyl radicals having from 1 to 12 carbon atoms, with at least one hydrocarbyl sulfoxide of the formula

wherein each R' may be the same or different alkyl radical having from 1 to 12 carbon atoms or wherein the two such R' groups are combined to form a cyclic ring containing the sulfur atom and at least 4 carbons in the cyclic ring, in the presence of a reaction promoting amount of at least one protonic acid, wherein the temperature, the pressure, said at least one ditertiary organic sulfide, said at least one hydrocarbyl sulfoxide and the amounts thereof are such that at least one ditertiary organic disulfide is produced.

2. A method according to claim 1 wherein each R is an alkyl radical.

3. A method according to claim 2 wherein said contacting is conducted at a temperature in the range of about 40° C. to about 250° C.

4. A method according to claim 3 wherein said contacting is done under an inert atmosphere.

5. A method according to claim 4 wherein the molar ratio of hydrocarbyl sulfoxide to ditertiary alkyl sulfide is in the range of about 20/1 to about 1/20.

6. A method according to claim 5 wherein said at least one protonic acid is selected from the group consisting of hydrochloric acid, hydrobromic acid, and hydroiodic acid.

7. A method according to claim 6 wherein said at least one hydrocarbyl sulfoxide is selected from the group consisting of dimethyl sulfoxide, diethyl sulfoxide, methyl ethyl sulfoxide, didodecyl sulfoxide, and tetramethylene sulfoxide.

8. A method according to claim 7 wherein said contacting is conducted in the presence of a diluent that is inert under the reaction conditions.

9. A method according to claim 8 wherein the ratio of the moles of protonic acid to the sum of the moles of hydrocarbyl sulfoxide and ditertiary alkyl sulfide is in the range of about 0.0001/1 to about 0.01/1.

10. A method according to claim 9 comprising the contacting of dimethyl sulfoxide and ditertiary butyl sulfide.

11. A method according to claim 10 wherein the molar ratio of dimethyl sulfoxide to ditertiary butyl sulfide is in the range of about 2/1 to about 5/1, the number of moles of diluent is no greater than about 5 times the sum of the moles of ditertiary butyl sulfide and dimethyl sulfoxide and no less than about 0.1 of that sum, the ratio of the moles of protonic acid to the sum of the moles of the dimethyl sulfoxide and the ditertiary butyl sulfide is in the range of about 0.001/1 to about 0.005/1, and the temperature is in the range of about 50° C. to about 150° C.

12. A method according to claim 11 wherein the protonic acid consists essentially of hydrochloric acid.

13. A method according to claim 12 wherein said contacting is conducted in the presence of at least one Lewis acid, said Lewis acid being present in an amount which increases the rate of the reaction.

14. A method according to claim 13 wherein the Lewis acid consists essentially of lead chloride.

15. A method comprising contacting at least one ditertiary organic sulfide of the formula

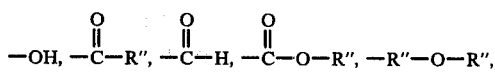

wherein each R may be the same or different radical selected from the group consisting of (1) hydrocarbyl radicals containing one or more substituents selected from the group consisting of

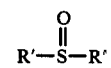
—OH, —C—R", —C—H, —C—O—R", —R"—O—R", and halogens, wherein R" is a hydrocarbyl radical having from 1 to 12 carbon atoms, and (2) hydrocarbyl radicals, with at least one hydrocarbyl sulfoxide of the formula

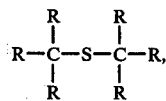

wherein each R' may be the same or different alkyl radical having from 1 to 12 carbon atoms or wherein the two such R' groups are combined to form a cyclic ring containing the sulfur atom and at least 4 carbons in the cyclic ring, in the presence of a reaction promoting amount of at least one protonic acid, wherein the temperature, the pressure, said at least one organic sulfide, said at least one hydrocarbyl sulfoxide and the amounts thereof are such that at least one ditertiary organic disulfide is produced.

16. A method comprising contacting at least one ditertiary organic sulfide of the formula

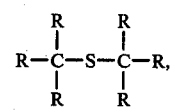

wherein each R may be the same or different hydrocarbyl radical, with at least one hydrocarbyl sulfoxide of the formula

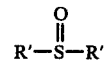

wherein each R' may be the same or different alkyl radical having from 1 to 12 carbon atoms or wherein the two such R' groups are combined to form a cyclic ring containing the sulfur atom and at least 4 carbons in the cyclic ring, in the presence of a reaction promoting amount of at least one protonic acid, said contacting being conducted at a temperature in the range of about 40° C to about 250° C under reaction conditions such that at least one ditertiary organic disulfide is produced.

* * * * *